United States Patent [19]

Rosenberg et al.

[11] Patent Number: 5,152,790
[45] Date of Patent: Oct. 6, 1992

[54] LIGAMENT RECONSTRUCTION GRAFT ANCHOR APPARATUS

[75] Inventors: Thomas D. Rosenberg, Salt Lake City, Utah; Gerard S. Carlozzi, Weymouth, Mass.; William J. Reimels, Brockton, Mass.

[73] Assignee: American Cyanamid Company, Stamford, Conn.

[21] Appl. No.: 672,893

[22] Filed: Mar. 21, 1991

[51] Int. Cl.⁵ .............................. A61F 2/08
[52] U.S. Cl. ........................... 623/13; 606/73
[58] Field of Search ............... 623/13, 17; 606/72, 606/73; 439/13, 22, 23

[56] References Cited

U.S. PATENT DOCUMENTS

| | | | |
|---|---|---|---|
| 3,953,896 | 5/1976 | Treace | 3/1 |
| 4,301,551 | 11/1981 | Dore et al. | 3/1 |
| 4,708,132 | 11/1987 | Silvestrini | 128/92 |
| 4,738,255 | 4/1988 | Goble et al. | 128/92 |
| 4,741,702 | 5/1988 | Yasumoto | 439/578 |
| 4,744,793 | 5/1988 | Parr et al. | 623/13 |
| 4,772,286 | 9/1988 | Goble et al. | 623/13 |
| 4,828,562 | 5/1989 | Kenna | 623/13 |
| 4,870,957 | 10/1989 | Goble et al. | 129/92 |
| 4,946,458 | 8/1990 | Harms et al. | 623/17 |
| 4,950,270 | 8/1990 | Bowman et al. | 606/72 |

Primary Examiner—Randy C. Shay
Attorney, Agent, or Firm—Douglas E. Denninger

[57] ABSTRACT

A ligament graft replacement system (10) having an anchor assembly (16) on one end. The anchor assembly (16) includes an insert member (18), a threaded sleeve (22) and a rotatable ring (20) to which the graft (24) is attached. A harvested or synthetic graft (24) used as a replacement for a torn ligament or tendon is secured to the rotatable ring (20) by sutures (46) and the anchor assembly (16) is screwed into a tunnel (26) drilled in a bone or bone-like structure. The anchor assembly (16) includes a hexagonal opening (36) through its length for receiving a hex driver (48) in its trailing end (36) or its leading end (34). The anchor assembly (16) also preferably has a self-tapping thread (30) on its outer surface. The rotatable ring (20) is secured over annular flange (40) at the trailing end of the threaded sleeve (22) and has a plurality of openings or slots (50) to which the sutures (46) are attached.

12 Claims, 2 Drawing Sheets

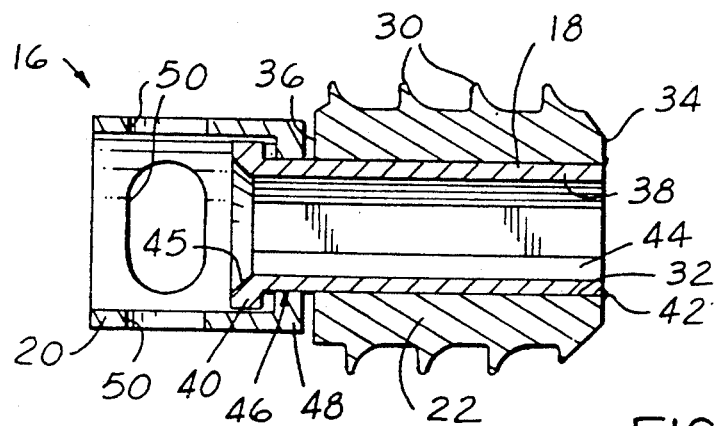
FIG.4
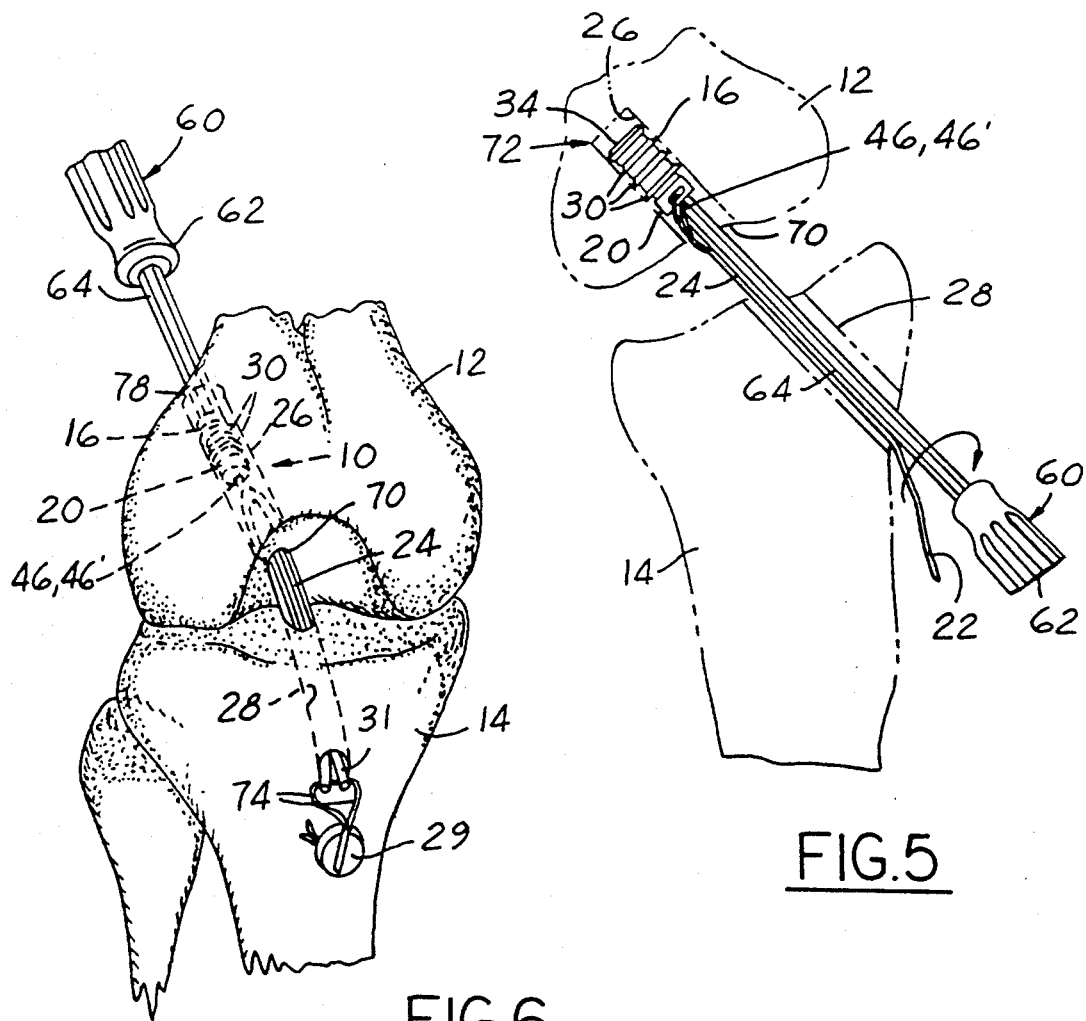
FIG.5
FIG.6

LIGAMENT RECONSTRUCTION GRAFT ANCHOR APPARATUS

TECHNICAL FIELD

The present invention relates to an improved device for fixating a replacement ligament which is received within a bore in a bone as well as an improved system for reconstruction of a torn ligament using arthroscopic surgical techniques.

BACKGROUND ART

Arthroscopic surgical procedures have vastly improved the ability of orthopedic surgeons to treat injuries to joints. An example of one such procedure is the replacement of anterior cruciate ligaments (ACL) of the knee. Torn or ruptured ligaments which may be caused by "sport injuries" (so referred to due to the frequency of knee injuries in sports such as football or skiing) may now be replaced by tendon grafts or artificial ligaments.

One of the problems involved in replacing ligaments, and particularly the ACL, is the need to provide a firm permanent fixation point for the replacement graft. It is important that the device or system for securing the graft be relatively easy to install with the aid of endoscopic techniques. An important feature of devices for fixing grafts to bones also includes the ability to adjust the device, if necessary, after installation. Similarly, the ability to initially control the depth of insertion of the fixation device is an important consideration.

With any fixation device or system for securing a ligament graft to a bone or bone-like structure, it is important not to damage the graft during installation. It is another objective of anchoring systems to minimize trauma. One way to minimize trauma is to limit the number and size of the access openings to the joint required for completion of the graft operation. By minimizing the number of openings, the time required for the procedure and for post operative recuperation is minimized.

In the past, ligament grafts were usually secured to bones by staples or screws. These types of devices are simple and effective, but typically require access to both ends of the ligament graft and also require longer lengths of graft tendons or artificial ligaments. These problems led to the development of other ligament anchor systems, such as that disclosed in U.S. Pat. No. 4,772,286. That patent discloses a ligament attachment method and apparatus having an artificial cruciate ligament with tensionable cone elements on one or both ends. Another embodiment disclosed in that patent discloses a process and device in which a rolled replacement tendon is sutured to a threaded cylinder which is installed with a hex driver.

Other known devices are disclosed in U.S. Pat. No. 4,870,957. That patent discloses a ligament anchor in which a two part device is provided on each end of the ligament. This device allows for a single entry point for placement of the ligament, but requires that a special spring clip be inserted into a previously secured threaded footing. A clip having a flared end is snapped into the installed footing. The clips are maneuvered with the tendon attached through holes in the femur and tibia in which the anchors have been previously set.

The devices and procedures discussed above are fairly time consuming and complicated to use and, if not carefully performed, could result in damage to the graft.

These and other problems are addressed by the present invention.

DISCLOSURE OF INVENTION

According to the present invention, a ligament anchor assembly is disclosed for securing a ligament graft in a tunnel or bore formed in a bone. In particular, the present invention relates to an anchor that is well-suited for arthroscopic ACL replacement surgery.

The ligament reconstruction graft anchor of the present invention includes an anchor assembly having a tool-receiving central opening, an external screw thread and a rotatable ring secured to one end. The graft ligament is sutured or otherwise secured to the rotatable ring.

The ligament graft system utilizing the unique anchor assembly is used in arthroscopic ACL replacement surgery. The system includes a graft ligament for installation between a patient's femur and tibia. The anchor assembly is secured in a bore in the patient's femur which has been formed in a precise location. The anchor has a threaded sleeve and a tool receiving central opening. (The central opening could also be formed in an insert member which is positioned in an axial bore in the threaded sleeve.) A rotatable ring is secured to one end of the threaded sleeve and the femoral end of the graft is secured to the ring. The tibial end of the graft is secured to the tibia by conventional means.

The anchor assembly is preferably formed in three pieces including an insert member affixed within the threaded sleeve, along with a rotatable ring. The insert member has a tool-receiving opening at one end which preferably extends through the entire length of the anchor from the trailing end to the distal end so it can be manipulatable by a driver from either end.

One end of the anchor assembly includes a groove adjacent a radially outwardly extending flange. One end of the rotatable ring is positioned in the groove and the ring is thus held securely on the anchor and is rotatable relative thereto.

The femoral end of the graft is affixed to the rotatable fastening ring preferably with sutures. The tibial end of the graft is preferably affixed to the tibia by any conventional means, such as sutures to a staple, surgical screw or another known anchor.

It is an object of the invention to provide an improved graft anchor for ligament reconstruction surgery which is inserted using endoscopic or arthroscopic techniques to replace a torn ACL.

It is a further object of the present invention to provide a graft anchor which is secured within a bone tunnel and preferably a femoral tunnel. The anchor is turned by a driver instrument into the femoral tunnel while the tendon graft or prosthesis ligament is secured to a loose ring and thus does not turn or rotate with the anchor.

Another object of the invention is to provide an anchor to which a graft may be preassembled prior to installation and installed without damage to the graft.

It is also an object of the invention to provide a firm permanent fixation point for a ligament graft. Still another object of the invention is to provide a graft anchor which is adjustable after installation.

BRIEF DESCRIPTION OF DRAWINGS

FIG. 4 is a cross-sectional view of the graft anchor assembly shown in FIG. 3;

FIG. 5 is a schematic perspective view showing the graft anchor being driven into femoral tunnel; and FIG. 6 is a schematic perspective view depicting adjustment of the graft anchor subsequent to implantation.

BEST MODE(S) FOR CARRYING OUT THE INVENTION

Figure 1:
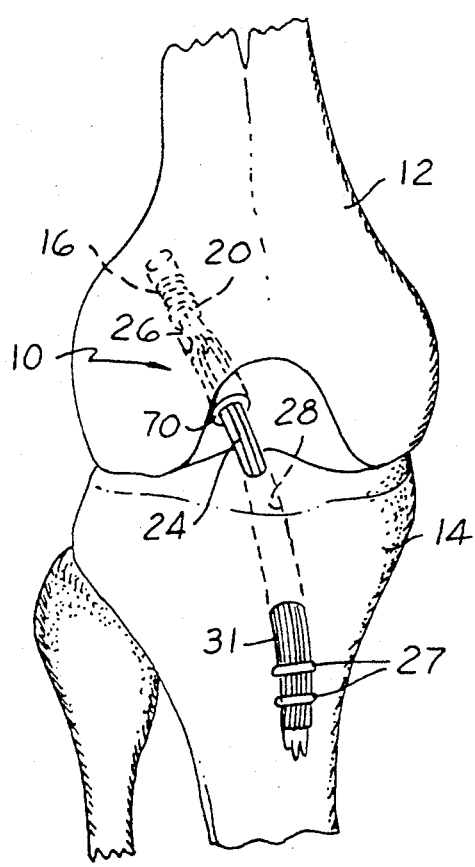
FIG. 1 is a schematic perspective view illustrating the positioning and securing of a tendon graft in accordance with the present invention.

The above and other objects of the invention are met by the inventive graft anchor system disclosed and claimed herein.

Referring now to FIGS. 1-5, a ligament graft replacement system 10 is shown for use as an anterior cruciate ligament (ACL) replacement. The ligament graft replacement system 10 extends between a femur 12 and a tibia 14 of a patient.

An anchor assembly 16 has an insert member 18, a rotatable ring 20 and a threaded sleeve member 22. A tendon graft 24 is secured at one end to the anchor assembly 16 (as described below) which is implanted in the femur 12, and is connected at its other end to the tibia 14. The anchor assembly 16 is screwed into a femoral tunnel 26, and the tendon graft 24 extends from the femoral tunnel 26 out through a tibial tunnel 28. The end 31 of the graft which exits from the tibial tunnel 28 can be attached to the tibia by any known method or mechanism such as, for example, surgical staples 27 (shown in FIG. 1) or a fixation screw 29 (shown in FIG. 6).

The insert member 18, threaded sleeve member 22 and ring member 20 are all preferably made of stainless steel, such as 316 LF-138 stainless. It is also possible for the anchor assembly members to be made from other equivalent materials, or from absorbable materials, such as polyglycolic acid or polylactic acid.

Figure 2:
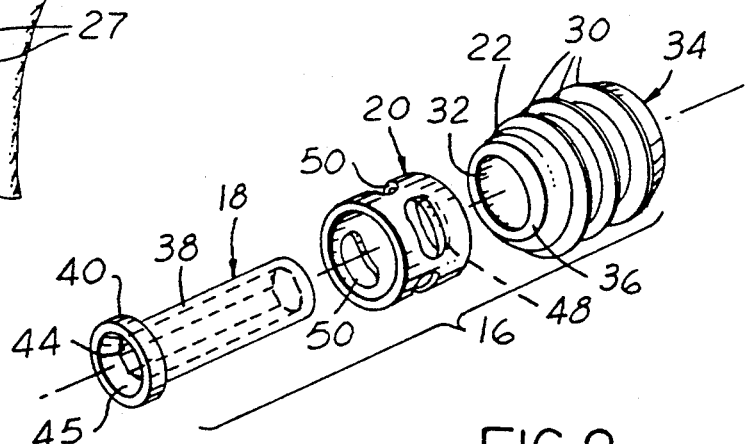
FIG. 2 is an exploded perspective view of a graft anchor assembly in accordance with the present invention.

Referring now to FIG. 2, the anchor assembly 16 will be described in more detail. The sleeve 22 has threads 30 on its outer surface and a cylindrical passageway or bore 32. The threads 30 are preferably self-tapping threads. The sleeve has a front or leading end 34 and trailing end 36.

The insert member 18 has a cylindrical body 38 and a flanged head 40 at one end. The outer diameter of the body 38 is dimensioned to form a press fit or sliding mating relationship with the bore or passageway 32 in the sleeve 22. When the insert member 18 is assembled in sleeve 22, they preferably are laser welded together at the front end (shown by reference numeral 42 in FIGS. 3 and 4).

The insert member 18 also includes a central driver or tool-receiving opening 44. The tool-receiving opening 44 is preferably a hexagonal-shaped opening which extends throughout the length of the sleeve 22. It is also possible for the central opening 44 of the insert member to have another cross-sectional shape, so long as it is sized or shaped to match the end of the driver instrument as explained below. It is also possible for the opening 44 to be a dead end bore not extending the entire length of the insert member. In addition, the opening 44 preferably has an angled or countersunk edge 45 which acts as a lead-in to more easily mate the anchor assembly with the driver. The flanged head 40 is formed to extend beyond the length of the sleeve member 22 forming an annular groove 46 situated between the head 40 and the trailing end 36 of the sleeve member 22.

The ring 20 is cylindrical with an inwardly extending annular flange or rim 48 at one end. A plurality of suture tie slots or openings 50 are provided around the circumference of the ring 20. The openings 50 allow for ease of tying or otherwise connecting the graft ligament 24 (or ligaments 24 and 24') to the anchor assembly 16.

When the anchor assembly is assembled, the ring member 20 is first assembled on the insert member 18, and then the insert member is inserted into the sleeve member 22 and welded in place. In this manner, the ring member 20 is prevented from being removed from, or falling off the anchor assembly 16, and is also allowed to rotate freely relative to the sleeve/insert member subcombination.

The graft ligaments 24 and 24' are shown attached to the ring 20 by sutures 46 and 46'. The sutures are connected to the tendon grafts by, for example, whip stitches, and then tied to the ring 20 through the openings 50. As indicated by the drawings, one or more grafts (24, 24', etc.) can be utilized with the present invention.

Figure 3:
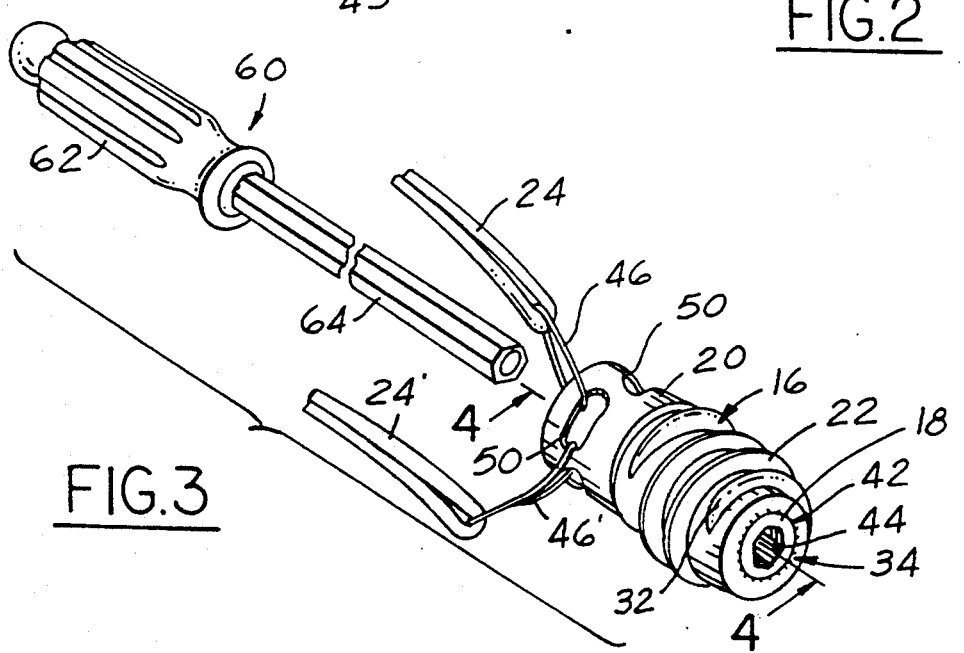
FIG. 3 illustrates an anchor assembly having a tendon sutured to the rotatable ring, together with a driver instrument.

A driver instrument 60 having a handle 62 and hexagonal-shaped shaft 64 is shown in FIG. 3. The end of the shaft 64 is dimensioned to fit within the opening 44 in the insert member 18 so the driver can be used to turn the anchor assembly 16 into position in the bone. Preferably, the driver 60 can be used to engage and turn the anchor assembly 16 from either the trailing end or the leading end.

The installation of the anchor assembly 16 is shown in FIG. 5. After the tibial tunnel 28 and femoral tunnel 26 are formed in the desired position by a conventional means and method, the driver instrument 60 is inserted into the central opening 44 in the anchor. In this regard, care should be taken not to damage the tendon grafts 24, 24'. The grafts are positioned and held firmly around the shaft 64 of the driver and the anchor-graft-driver assembly is inserted into the joint through the tibial tunnel. (In this regard, the tibial tunnel should be made larger in diameter than the femoral tunnel and slightly larger than the outside diameter of the threaded sleeve member 22.)

Once the anchor assembly contacts the femoral tunnel opening 70, the driver instrument 60 is turned (rotated) and the anchor is screwed into position. The self-tapping threads 30 turn into the bone in the femoral tunnel firmly holding the graft in position. Due to the assembly of the ring 20 on the anchor, the ring 20 and graft 24, 24' do not rotate or twist in the tunnels when the anchor assembly is being screwed into position. This prevents possible damage to the graft.

As is evident from the above description of the method of operation, the present invention has particular use in and facilitates the use of a "blind-end" femoral tunnel technique of ACL reconstruction surgery. Such a technique is disclosed, for example, in co-pending application Ser. No. 472,724, filed on Jan. 31, 1990, which is owned by the same assignee as the present case. That application and its disclosure and contents are hereby incorporated by reference. With this technique, all of the procedural steps for determining the site for the femoral tunnel, drilling the femoral tunnel, and implanting the graft are carried out through the tibial tunnel. It is not necessary to make a lateral femoral incision or perform any of the rear entry techniques. As shown in FIG. 5, the femoral tunnel 26 only extends to point 72.

As mentioned above, an alternative method of fixating the trailing end 31 of the tendon graft 24 which extends out of the tibial tunnel 28 is shown in FIG. 6. In this embodiment, sutures 74 are attached to the end 31 of the graft, and the sutures are secured tightly around a surgical bone screw 29. Preferably, the screw 29 has a washer under its head in order to more securely hold the sutures in place.

FIG. 6 also discloses a technique for adjustment or removal of the anchor assembly after implanting of the graft 24. Adjustment might be necessary, for example, to later tighten the graft after the initial operation has been completed. If such adjustment of the positioning or tension of the tendon graft 24 is necessary, or if such removal is required, it is possible to access the anchor assembly 16 from the upper end 78 of the femoral tunnel 26. If the tunnel 26 is not drilled entirely through the femur initially (during the implanting operation), then it can be completed through a lateral incision. The driver 60 is then inserted through the upper end of the tunnel and into the tool-receiving opening 44 at the leading end 34 of the anchor assembly 16. In this manner, the anchor assembly 16 may be rotated to adjust the anchor assembly 16 within the femoral tunnel 26 without twisting or adversely affecting the tendon graft 24, or to remove it entirely.

The preferred tendon graft 24 is a semitendinous tendon which has been harvested from the patient, cut and cleaned, and doubled over and tied to the anchor ring 20. It is also possible to use the anchor assembly 16 of the present invention in conjunction with an artificial graft ligament, several harvested grafts, or many of the well-known synthetic or harvested grafts known in the art.

Although the present invention has been described relative to use of a three-part anchor assembly 16, it is also possible within the scope of the invention to provide a two-part assembly. In such a device, the sleeve member would be manufactured with an annular groove and flange at its trailing end and the insert member would be eliminated. The ring member would be snapped onto or formed over the flange so that the annular ridge 48 would fit within and be able to freely rotate in the groove. The technique for implanting such a device would be the same as that described above with respect to the three-part anchor assembly 16.

The preceding description of the preferred embodiments of the present invention is intended to be illustrative of preferred forms of the invention. It is anticipated that other modifications and enhancements of the present invention will be apparent based upon the above description. The scope of the present invention should be measured by the following claims, and not limited by the above description of the preferred embodiments.

I claim:

1. A ligament reconstruction graft anchor assembly for securing a graft ligament to a bone having a tunnel formed therein, comprising:
   a body member having a first end, a second end, a central opening and an external screw thread;
   graft fixation means secured to said first end of said body member, said graft fixation means being rotatable relative to said body member; and
   said body member having means for receiving a driver, said means for receiving extending through said body member from said first end to said second end.

2. An anchor assembly for securing a replacement ligament graft in an opening in a bone structure, said anchor assembly comprising:
   a sleeve member having a first end and a second end, an axial extending passageway therein and an external screw thread;
   an insert member positioned in said passageway and secured to said sleeve member, said insert member having means for receiving a driver at both of its ends; and
   a ring member rotatably affixed to said insert member, said ring member having graft fastening means thereon.

3. The anchor assembly of claim 2 further comprising annular groove means formed in said anchor assembly between said sleeve member and said insert member, and wherein said ring member is rotatably affixed in said groove means.

4. A graft anchor assembly for securing a graft to a bone having a tunnel formed therein, comprising:
   a body member having a first end, a second end, and an external screw thread;
   graft fixation means secured to said first end of said body member, said graft fixation means being rotatable relative to said body member and including fastening means for enabling the graft to be fixedly attached to said graft fixation means; said graft fixation means comprising continuously cylindrical ring means integrally and rotatably coupled to said body member;
   means for engaging a driver to enable rotatable placement of said body member in the bone tunnel while said graft fixation means is rotatably secured to said body member and the graft is fixedly attached to said graft fixation means to minimize torquing the graft; and
   said first end of said body member comprising flange means and said graft fixation means including holding means positioned over said flange means, said holding means including a rim of said ring means which extends radially inwardly to slidably engage said body member.

5. The anchor assembly of claim 4 wherein said rim slidably engages said body member between said flange means and said external screw thread.

6. The anchor assembly of claim 4 wherein said fastening means includes a plurality of slots formed in a side wall of said ring means to enable fastening of the graft to said ring means using suture means.

7. A graft anchor assembly for securing a graft to a bone having a tunnel formed therein, comprising:
   a body member having a first end, a second end, and an external screw thread;
   graft fixation means secured to said first end of said body member, said graft fixation means being rotatable relative to said body member and including fastening means for enabling the graft to be fixedly attached to said graft fixation means;
   means for engaging a driver to enable rotatable placement of said body member in the bone tunnel while said graft fixation means is rotatably secured to said body member and the graft is fixedly attached to said graft fixation means to minimize torquing the graft;

said first end of said body member comprising flange means and said graft fixation means includes holding means positioned over said flange means; and said graft fixation means comprising continuously cylindrical ring means integrally and rotatably coupled to said body member, said ring means defining a central passageway to enable insertion of the driver therethrough.

8. The anchor assembly of claim 7 wherein said screw thread is a self-tapping thread.

9. A graft anchor assembly for securing a graft to a bone having a tunnel formed therein, comprising:

a body member having a first end, a second end, and an external screw thread;

graft fixation means secured to said first end of said body member, said graft fixation means being rotatable relative to said body member and including fastening means for enabling the graft to be fixedly attached to said graft fixation means;

means for engaging a driver to enable rotatable placement of said body member in the bone tunnel while said graft fixation means is rotatably secured to said body member and the graft is fixedly attached to said graft fixation means to minimize torquing the graft; and an insert member positioned in said body member, said insert member having flange means thereon positioned at said first end of said body member for securing said graft fixation means.

10. The anchor assembly of claim 9 wherein said insert member defines therein said means for engaging a driver.

11. The anchor assembly of claim 10 wherein said graft fixation means comprises cylindrical ring means having a rim which extends radially inwardly to slidably engage said insert member, and said ring means defining a central passageway to enable insertion of the driver therethrough to engage said means for engaging.

12. A method of implanting a replacement graft ligament between a patient's femur and tibia, said method comprising the steps of:

forming a first tunnel in the tibia;

forming a second tunnel in the femur;

providing an anchor assembly having a body member including an external screw thread and having graft fixation means rotatably secured to an end of said body member;

attaching a first end of the graft ligament to said graft fixation means;

positioning said anchor assembly with the graft ligament attached thereto into the second tunnel by rotating said body member into the second tunnel without substantially imparting rotation to said graft fixation means and the attached graft ligament; and securing the other end of the graft ligament in the first tunnel or outside the first tunnel on the tibia.

* * * * *